United States Patent
Han et al.

(10) Patent No.: US 8,057,714 B2
(45) Date of Patent: Nov. 15, 2011

(54) SYNTHESIS METHOD OF METAL CYCLOPENTADIENIDE IN BULK

(75) Inventors: Yong gyu Han, Daejeon (KR); Ki-soo Lee, Daejeon (KR); Heon-yong Kwon, Daejeon (KR); Jong-sang Park, Daejeon (KR); Nicola Maggiarosa, Cologne (DE)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 12/515,819

(22) PCT Filed: Nov. 2, 2007

(86) PCT No.: PCT/KR2007/005511
§ 371 (c)(1),
(2), (4) Date: Dec. 10, 2009

(87) PCT Pub. No.: WO2008/062958
PCT Pub. Date: May 29, 2008

(65) Prior Publication Data
US 2010/0096762 A1    Apr. 22, 2010

(30) Foreign Application Priority Data
Nov. 23, 2006    (KR) .................. 10-2006-0116579

(51) Int. Cl.
*C07F 1/00*    (2006.01)

(52) U.S. Cl. .................... 260/665 R; 585/350; 585/353; 585/354

(58) Field of Classification Search ............. 260/655 R, 260/665 R; 585/350, 353, 354
See application file for complete search history.

(56) References Cited

U.S. PATENT DOCUMENTS

| | | | | |
|---|---|---|---|---|
| 2,942,040 A | * | 6/1960 | Odenweller et al. | 260/665 R |
| 3,152,157 A | * | 10/1964 | Shapiro et al. | 556/58 |
| 3,306,917 A | * | 2/1967 | Shapiro et al. | 556/143 |
| 4,547,603 A | | 10/1985 | Rajan | |
| 4,952,713 A | | 8/1990 | Lilga et al. | |
| 5,585,509 A | | 12/1996 | Langhauser et al. | |
| 6,261,482 B1 | * | 7/2001 | Wietelmann et al. | 260/665 R |

FOREIGN PATENT DOCUMENTS
EP    0926150 A2    6/1999

OTHER PUBLICATIONS

Lide, et al., CRC Handbook of Chemistry and Physics, 91st edition, 2011 Internet Version, D. R. Lide, ed.*
Flick, Industrial Solvents Handbook, 5th edition, 1998, available on-line at www.knovel.com.*
Panda, et al., An Improved Synthesis of Sodium and Potassium Cyclopentadienide, Organometallics, 2003, 22(4), 877-878.*
International Search Report, PCT/KR2007/005511, dated Feb. 11, 2008.
Panda et al., Organometallics, 22; 877-878 (2003).
Shirokii et al., Zhurnal Obshchei Khimii, 53(8); 1892-1895 (1983).
Panda et al., Organometallics 2003, 22, 877-878.

* cited by examiner

*Primary Examiner* — In Suk Bullock
*Assistant Examiner* — Bradley Etherton
(74) *Attorney, Agent, or Firm* — Lerner, David, Littenberg, Krumholz & Mentlik, LLP

(57) ABSTRACT

The present invention relates to a synthesis method of metal cyclopentadienide by direct reaction of dicyclopentadiene with a group 1 metal in the presence of an aprotic solvent. Unlike the conventional method depending on retro Diels-Alder reaction of dicyclopentadiene to generate indirectly cyclopentadiene, the method of the present invention favors generation of cyclopentadiene and metal cyclopentadienide as well by adding dicyclopentadiene directly when the reaction temperature reaches to the boiling point of a reaction solvent.

6 Claims, No Drawings

SYNTHESIS METHOD OF METAL CYCLOPENTADIENIDE IN BULK

TECHNICAL FIELD

The present invention relates to a synthesis method of metal cyclopentadienide, more precisely a synthesis method of metal cyclopentadienide in bulk by reacting dicyclopentadiene directly with a group 1 metal using an aprotic solvent.

BACKGROUND ART

Metal cyclopentadienide generally indicates potassium cyclopentadienide ($KC_5H_5$) or sodium cyclopentadienide ($NaC_5H_5$).

The potassium cyclopentadienide was first synthesized by the reaction of cyclopentadiene (Cp) and potassium (K) 100 years ago. In general, the potassium cyclopentadienide can be synthesized by reacting cyclopentadiene with potassium metal in the presence of tetrahydrofuran (THF), benzene or liquid ammonia.

The synthesis of the sodium cyclopentadienide was first reported by K. Ziegler and E. O. Fisher. And the synthesis of the sodium cyclopentadienide these days is largely induced by the reaction of cyclopentadiene and NaOH, tert-NaOtBu or NaCl.

The conventional synthesis methods all use cyclopentadiene as a reactant. The cyclopentadiene is in equilibrium with dicyclopentadiene and most of the time it remains as dicyclopentadiene at room temperature.

So, the cyclopentadiene is generally obtained from dicyclopentadiene by retro Diels-Alder reaction at 170° C. However, the synthesis method of metal cyclopentadienide by the retro Diels-Alder reaction using the dicyclopentadiene as a reactant has such problems that it is difficult to control the Diels-Alder reaction with cyclopentadiene, suggesting that dicyclopentadiene might still remain, and a process of producing cyclopentadiene has to be included, making the procedure complicated.

There has been an attempt to synthesize metal cyclopentadiene not by the indirect reaction with cyclopentadiene but by direct reaction with dicyclopentadiene.

Particularly, it has been tried to synthesize metal cyclopentadienide using dicyclopentadiene as a reactant in a high temperature/high pressure reactor or by the reaction with sodium metal in the presence of iron at room temperature or at 170° C.

However, the synthesis of metal cyclopentadienide using the high temperature/high pressure reactor or via reaction using iron as a catalyst does not favor mass-production.

As an alternative, a method to react dicyclopentadiene (as a reactant and reaction solvent) directly with sodium or potassium was reported in Organometallics 2003, 22, 877-878. However, this method also has a problem of over-dose of dicyclopentadiene which is necessarily used for mass-production but has to be eliminated.

DISCLOSURE OF INVENTION

Technical Problem

It is an object of the present invention, to overcome the above problems of the conventional methods, to provide a synthesis method of metal cyclopentadienide by direct reaction of dicyclopentadiene with a group 1 metal in the presence of an aprotic solvent.

Technical Solution

The above object of the present invention can be achieved by the following embodiments of the present invention.

The present invention is described in detail hereinafter.

To achieve the above object, the present invention provides a synthesis method of metal cyclopentadienide comprising the following steps:

i) adding an aprotic solvent represented by the following formula 1 wherein, $R_1$ and $R_4$ are substituted or unsubstituted C1-C4 alkyl group, $R_2$ and $R_3$ are substituted or unsubstituted C1-C4 ethylene group, and n and m are equal or different integers between 1-100, and a group I metal to a reactor and raising the temperature to the boiling point of the aprotic solvent; and

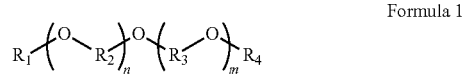

Formula 1 ii) adding dicyclopentadiene to the reactor to induce reaction.

The present invention provides a synthesis method of metal cyclopentadienide, in which the aprotic solvent represented by formula 1 and a group I metal are reacted in a reactor and dicyclopentadiene is added when the temperature of the reaction mixture reaches to the boiling point of the aprotic solvent and thereby the dicyclopentadiene is converted into cyclopentadiene by the aprotic solvent and further reacted with the group I metal added ahead of time.

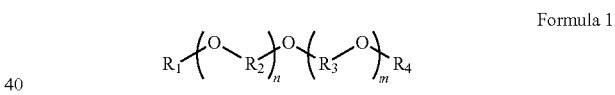

Formula 1 wherein, $R_1$ and $R_4$ are substituted or unsubstituted C1-C4 alkyl group, $R_2$ and $R_3$ are substituted or unsubstituted C1-C4 ethylene group, and n and m are equal or different integers between 1-100.

The aprotic solvent herein is preferably an ether based compound having the boiling point of 130-300° C., which favors the conversion of dicyclopentadiene into cyclopentadiene that requires at least the temperature of 130° C. If a solvent with boiling point of over 300° C. is used, it is not easy to raise the reaction temperature to that boiling point.

The aprotic solvent is exemplified by diethylene glycol dimethylether (diglyme), diethylene glycol dibutyl ether and diethylene glycol diethylether. Among them, the diethylene glycol dimethylether (diglyme) represented by formula 2 is preferred.

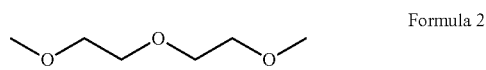

Formula 2

The synthesis process of the metal compound of cyclopentadienyl using the diglyme is as indicated in the following reaction formula 1.

[Reaction Formula 1]

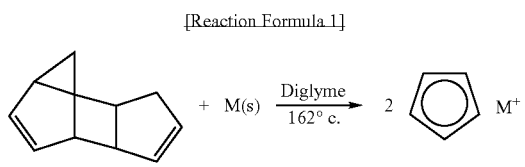

(Wherein, M is a group 1 metal.)
The group 1 metal is potassium (K) or sodium (Na).

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

Preparation of Sodium Cyclopentadienide (NaCp)

To a 10 L reactor were added 4 L of diglyme and 229 g of sodium (10 mole) stepwise. The temperature of the reactor was raised to the boiling point of diglyme (162° C.). After stabilizing the reaction temperature, 462 g (7 mole) of dicyclopentadiene was slowly added to the reaction solution. Then, white smoke was generated from the surface of the solution. Upon completion of the addition of dicyclopentadiene, reaction was confirmed by measuring hydrogen gas generation. When hydrogen gas generation was stopped, the reaction was terminated. The resultant solution was cooled down to room temperature. A sample was taken and tested for NaCp generation by NMR.

$^1$H-NMR (400.13 MHz, $C_6D_6$, ppm): $\delta$=5.60; $^{13}$C-NMR (120.62 MHz, $C_6D_6$, ppm): $\delta$=94.9.

Example 2

Preparation of Potassium Cyclopentadienide (KCp)

An experiment was performed by the same manner as described in example 1, except that 391 g (10 mole) of potassium was used instead of 229 g (10 mole) of sodium. The resultant solution was cooled down to room temperature. A sample was taken and tested for KCp generation by NMR.

$^1$H-NMR (400.13 MHz, $C_6D_6$, ppm): $\delta$=5.60; $^{13}$C-NMR (120.62 MHz, $C_6D_6$, ppm): $\delta$=94.9.

Comparative Example 1

Preparation of Sodium Cyclopentadienide (NaCp)

Dicyclopentadiene was converted into cyclopentadiene by retro Diels-Alder reaction at 172° C. To a 10 L reactor was added 6 L of THF and then 229 g (10 mole) of sodium was added thereto. 462 g (14 mole) of cyclopentadiene was slowly added to the reaction solution. Hydrogen gas generation was confirmed by using an oil bubbler. Upon completion of the addition of cyclopentadiene, hydrogen gas generation was checked by observing the oil bubbler. When hydrogen gas generation was stopped, the reaction was terminated. The generation of NaCp was confirmed by NMR.

$^1$H-NMR (400.13 MHz, $C_6D_6$, ppm): $\delta$=5.60; $^{13}$C-NMR (120.62 MHz, $C_6D_6$, ppm): $\delta$=94.9.

As explained in examples, cyclopentadiene and metal cyclopentadienide were synthesized by direct addition of dicyclopentadiene at the boiling temperature of a reaction solvent. This method was confirmed to be simpler and easier than the method of comparative example in which cyclopentadiene was prepared by retro Diels-Alder reaction of dicyclopentadiene.

INDUSTRIAL APPLICABILITY

The present invention relates to a synthesis method of metal cyclopentadienide. According to this method, unlike the conventional method which is indirect cyclopentadiene synthesis via retro Diels-Alder reaction of dicyclopentadiene, dicyclopentadiene is directly added when the reaction temperature reaches the boiling point of a reaction solvent and thus cyclopentadiene and metal cyclopentadienide are simultaneously generated during the reaction, suggesting that the method of the invention is much more efficient.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A synthesis method of metal cyclopentadienide comprising:
   i) adding diethylene glycol dimethylether or diethylene glycol dibutyl ether as an aprotic solvent and a group I metal to a reactor and raising a reaction temperature to the boiling point of the aprotic solvent, and
   ii) adding dicyclopentadiene to the reactor after the reaction temperature of the step i) stabilizes at the boiling point of the aprotic solvent to induce reaction.

2. The synthesis method of metal cyclopentadienide according to claim 1, wherein the group I metal is potassium or sodium.

3. The synthesis method of metal cyclopentadienide according to claim 1, wherein the amount of the aprotic solvent added is 4 L, the amount of the group I metal added is 10 moles, and the amount of the dicyclopentadiene added is 7 moles.

4. A synthesis method of metal cyclopentadienide comprising:
   i) adding an aprotic solvent represented by the following Formula 1 and a group I metal, selected from the group consisting of lithium, potassium, rubidium, cesium, and francium, to a reactor and raising a reaction temperature to the boiling point of the aprotic solvent, wherein the aprotic solvent has the boiling point between 130° C. to 300° C.

Formula 1

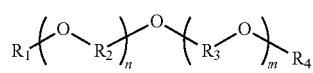

wherein $R_1$ and $R_4$ are substituted or unsubstituted C1-C4 alkyl groups, $R_2$ and $R_3$ are substituted or unsubstituted C1-C4 ethylene groups and n and m are equal or different integers between 1-100; and ii) adding dicyclopentadiene to the reactor after the reaction temperature of the step i) stabilizes at the boiling point of the aprotic solvent to induce reaction.

5. The synthesis method of metal cyclopentadienide according to claim 4, wherein the aprotic solvent is diethylene glycol dimethylether, diethylene glycol dibutyl ether or diethylene glycol diethylether.

6. The synthesis method of metal cyclopentadienide according to claim 4, wherein the group I metal is potassium.

* * * * *

UNITED STATES PATENT AND TRADEMARK OFFICE
CERTIFICATE OF CORRECTION

PATENT NO. : 8,057,714 B2
APPLICATION NO. : 12/515819
DATED : November 15, 2011
INVENTOR(S) : Yonggyu Han et al.

Page 1 of 1

It is certified that error appears in the above-identified patent and that said Letters Patent is hereby corrected as shown below:

On the title page in Inventor item (75), "Yong gyu Han" should read --Yonggyu Han--.
Column 2, line 13, "alkyl group" should read --alkyl groups--.
Column 2, line 13, "ethylene group" should read --ethylene groups--.
Column 2, line 44, "alkyl group" should read --alkyl groups--.
Column 2, line 45, "ethylene group" should read --ethylene groups--.
Column 2, line 47, "ether based" should read --ether-based--.

Signed and Sealed this
Twelfth Day of March, 2013

Teresa Stanek Rea
*Acting Director of the United States Patent and Trademark Office*